United States Patent [19]

Woodard

[11] Patent Number: 4,535,194

[45] Date of Patent: Aug. 13, 1985

[54] PROCESS FOR PRODUCING 1,1,2,3-TETRACHLOROPROPENE

[75] Inventor: Scott S. Woodard, Maryland Heights, Mo.

[73] Assignee: Monsanto Co., St. Louis, Mo.

[21] Appl. No.: 511,131

[22] Filed: Jul. 6, 1983

[51] Int. Cl.$^3$ .............................................. C07C 17/00
[52] U.S. Cl. ................................... 570/236; 570/220; 570/257; 570/228; 570/229; 570/253
[58] Field of Search ............... 570/257, 220, 228, 229, 570/253, 236

[56] References Cited

U.S. PATENT DOCUMENTS

| | | | |
|---|---|---|---|
| 2,420,975 | 5/1943 | Plump | 570/253 |
| 2,561,516 | 7/1951 | Ladd et al. | 570/229 |
| 2,593,451 | 4/1952 | Hill et al. | 570/228 |
| 2,658,930 | 11/1953 | Thompson | 570/257 |
| 3,639,493 | 2/1972 | Campbell | 570/228 |
| 3,926,758 | 12/1975 | Smith | 204/163 R |

FOREIGN PATENT DOCUMENTS

| | | | |
|---|---|---|---|
| B 36503 | 10/1956 | Fed. Rep. of Germany | 570/257 |
| 3007634 | 9/1981 | Fed. Rep. of Germany | 570/228 |
| 49-66613 | 6/1974 | Japan . | |
| 340812 | 10/1959 | Switzerland | 570/257 |
| 899523 | 1/1982 | U.S.S.R. . | |

OTHER PUBLICATIONS

Haszeldine, "Fluoro-olefins, Part II, Synthesis and Reaction of Some 3,3,3-Trihalogenopropenes", J. Chem. Soc. (1953) pp. 3371-3378.

Asahara, "The Telomerization of Carbon Tetrachloride and Ethylene", Kogyo Kagaku Zasshi (1971), 74 (4), 703-705.

Nesmeyanov et al., Doklady Akad. Nauk. S.S.S.R., 1951, 78, 717; Chem. Abs., 1952, 46, 1957).

Primary Examiner—Charles F. Warren
Assistant Examiner—Joseph A. Boska
Attorney, Agent, or Firm—J. Timothy Keane; Richard H. Shear

[57] ABSTRACT

A process is disclosed for preparing 1,1,2,3-tetrachloropropene comprising allylic rearrangement of 2,3,3,3-tetrachloropropene using a substantially anhydrous ferric chloride catalyst. Alternatively, 1,1,2,3-tetrachloropropene is prepared by dehydrochlorination of 1,1,1,2,3-pentachloropropane using a ferric chloride catalyst. Process schemes commencing with the preparation of the precursor 1,1,1,3-tetrachloropropane by reaction of ethylene with carbon tetrachloride are also disclosed.

6 Claims, No Drawings

PROCESS FOR PRODUCING 1,1,2,3-TETRACHLOROPROPENE

BACKGROUND OF THE INVENTION

This invention relates to the preparation of 1,1,2,3-tetrachloropropene and, more particularly, to novel methods for such preparation involving allylic rearrangement of 2,3,3,3-tetrachloropropene or dehydrochlorination of 1,1,1,2,3-pentachloropropane.

1,1,2,3-tetrachloropropene ("Tetra") is an important chemical intermediate useful, for example, in the preparation of the herbicide trichloroallyl diisopropyl thiocarbamate, commonly referred to as "triallate". Conventionally, Tetra is produced by dehydrochlorination of 1,1,2,2,3-pentachloropropane that is produced in turn by chlorination of 1,2,3-trichloropropene. While this process provides a generally satisfactory technical route, the cost of producing the tetrachloropropene depends upon the cost of the trichloropropene raw material.

Smith U.S. Pat. No. 3,926,758 describes an alternative route to 1,1,2,3-tetrachloropropene in which 1,2,3-trichloropropane is chlorinated in an open vessel exposed to u.v. light to produce a mix of chlorinated products containing 20% to 60% by weight unreacted 1,2,3-trichloropropane. The chlorinator effluent is separated into five fractions, one of which contains 1,1,1,2,3- and 1,1,2,2,3-pentachloropropanes. Another fraction containing 1,1,2,3-tetrachloropropane is dehydrochlorinated and then rechlorinated to produce a further fraction containing 1,1,1,2,3- and 1,1,2,2,3-pentachloropropanes. These two pentachloropropane fractions are mixed and subjected to dehydrochlorination to provide a mix of 1,1,2,3- and 2,3,3,3-tetrachloropropenes which is fed to an isomerizer packed with siliceous granules in which the 2,3,3,3-isomer is converted to the 1,1,2,3-isomer.

U.S.S.R. Inventor's Certificate No. 899,523 describes a somewhat modified process in which 1,2,3-trichloropropane is chlorinated to produce tetrachloropropanes; 1,1,2,3- and 1,2,2,3-tetrachloropropanes are extracted from the reaction mixture and further chlorinated in the presence of dimethylformamide as an initiator to produce pentachloropropanes; 1,1,1,2,3- and 1,1,2,2,3-pentachloropropanes are extracted from the pentachloropropane mixture and dehydrochlorinated to produce a mixture of 1,1,2,3- and 2,3,3,3-tetrachloropropenes; and the latter mixture is boiled in the presence of aluminum oxide (attapulgite) to isomerize the 2,3,3,3- to the 1,1,2,3- isomer. An overall yield of 48.19% is reported. The reference describes as prior art a process very close to that of Smith.

An earlier reference by Haszeldine, "Fluoro-olefins. Part II. Synthesis and Reaction of Some 3,3,3-Trihalogenopropenes" Journal of the Chemical Society [1953] pp. 3371–3378, describes a plethora of reactions of products derived from 1,1,1,3-tetrachloropropane. The reference describes preparation of this intermediate by reaction of carbon tetrachloride with ethylene in the presence of benzoyl peroxide. Among the numerous syntheses carried out by Haszeldine with 1,1,1,3-tetrachloropropane as the starting material are: dehydrochlorination of this starting material with 10% ethanolic potassium hydroxide to produce a mixture of 3,3,3- and 1,1,3-trichloropropene; isomerization of 3,3,3-trichloropropene to 1,1,3-trichloropropene using a variety of allylic rearrangement catalysts including antimony fluoride, concentrated hydrochloric acid, concentrated sulfuric acid, aluminum chloride, ferric chloride, ethanolic KOH and anhydrous hydrogen fluoride; chlorination of 1,1,3-trichloropropene in the presence of light to produce 1,1,1,2,3-pentachloropropane; chlorination of 3,3,3-trichloropropene to produce 1,1,1,2,3-pentachloropropane; dehydrochlorination of 1,1,1,2,3-pentachloropropane with ethanolic potassium hydroxide to produce a mixture of 2,3,3,3-tetrachloropropene and 1,1,2,3-tetrachloropropene; separation of 2,3,3,3-tetrachloropropene from 1,1,2,3-tetrachloropropene by distillation; and isomerization of 2,3,3,3-tetrachloropropene in the presence of aluminum chloride to produce 1,1,2,3-tetrachloropropene in 51% yield. Alternatively, Haszeldine discloses thermal isomerization of 2,3,3,3-tetrachloropropene to 1,1,2,3 tetrachloropropene at 180° C. in 45% yield. Based on the yields reported by Haszeldine for the above described series of steps, the overall yield obtained with his syntheses can be computed as 41.8% based on 1,1,1,3-tetrachloropropane, 10.4% based on carbon tetrachloride.

Asahara et al., "The Telomerization of Ethylene and Carbon Tetrachloride", Kogyo Kagaku Zasshi 1971, 74(4), 703–5 discloses telomerization of ethylene and carbon tetrachloride at 130° C. and at 60–70×10$^5$ Pa (60–70 atmospheres) pressure in the presence of a triethyl phosphite-ferric chloride hexahydrate catalyst to produce 1,1,1,3-tetrachloropropane. Takamizawa et al. U.S. Pat. No. 4,243,607 describes an improvement in the Asahara process whereby higher yields of 1,1,1,3-tetrachloropropane are obtained by utilizing a catalyst system comprising a nitrile in addition to an iron salt and a trialkyl phosphite.

Japanese Kokai No. 74-66613 describes a process for producing 1,1,3-trichloropropene by dehydrochlorination of 1,1,1,3-tetrachloropropane using anhydrous FeCl$_3$ as a catalyst. Reaction is carried out using 0.2 to 0.6 g FeCl$_3$ per mole of 1,1,1,3-tetrachloropropane at a temperature of 80° C. to 100° C.

A need has remained in the art for improved processes for the synthesis of 1,1,2,3-tetrachloropropene, especially processes which provide this product in high yield using relatively inexpensive starting materials and which can be operated at modest manufacturing costs.

SUMMARY OF THE INVENTION

Briefly, the present invention is directed to a process for producing 1,1,2,3-tetrachloropropene by contacting 2,3,3,3-tetrachloropropene with a catalytic proportion of substantially anhydrous ferric chloride, thereby effecting isomerization of the 2,3,3,3-tetrachloropropene to 1,1,2,3-tetrachloropropene via an allylic rearrangement reaction.

The invention is further directed to a process for producing 1,1,2,3-tetrachloropropene in which 1,1,1,3-tetrachloropropane is prepared by reaction of ethylene with carbon tetrachloride in the presence of both a source of metallic iron that is effective as an activator for the reaction, and a promoter for the reaction. The promoter is a trialkyl phosphite or a phosphorus (V) compound containing a phosphoryl group. The 1,1,1,3-tetrachloropropane is dehydrochlorinated to produce a mixture of 1,1,3- and 3,3,3-trichloropropene, and at least one of the trichloropropene isomers obtained by said dehydrochlorination is chlorinated to produce 1,1,1,2,3-pentachloropropane. The pentachloropropane is dehydrochlorinated to produce a mixture of 1,1,2,3- and 2,3,3,3-tetrachloropropenes; and the mixture of tetrachloropropenes is contacted with a Lewis acid allylic rearrangement catalyst, thereby converting the 2,3,3,3-tetrachloropropene content thereof to 1,1,2,3-tetrachloropropene.

The invention is also directed to a process for producing 1,1,2,3-tetrachloropropene by contacting 1,1,1,2,3-pentachloropropane with a catalytic proportion of ferric chloride to effect dehydrochlorination of the 1,1,1,2,3-pentachloropropane to produce 1,1,2,3-tetrachloropropene.

The invention is further directed to a process in which 1,1,1,2,3-pentachloropropane is prepared in the manner described above, and the pentachloropropane is dehydrochlorinated to 1,1,2,3-tetrachloropropene using a ferric chloride catalyst.

DESCRIPTION OF THE PREFERRED EMBODIMENTS

In accordance with the present invention, novel processes have been discovered by which 1,1,2,3-tetrachloropropene (Tetra) can be produced with significantly lower manufacturing costs than have been attainable with previously known commercial processes. Moreover, the processes of this invention provide improved efficiency and yields as compared to other known prior art processes based on 1,1,1,3-tetrachloropropane. 1,1,2,3-tetrachloropropene produced in accordance with the processes of the invention is of high quality, suitable for use in manufacture of herbicides, pharmaceuticals and other end products.

In accordance with a preferred embodiment of the invention, 1,1,2,3-tetrachloropropene (Tetra) is prepared in a four step synthesis from 1,1,1,3-tetrachloropropane that is in turn produced by a reaction of ethylene and carbon tetrachloride.

In the preparation of the 1,1,1,3-tetrachloropropane, ethylene is reacted with carbon tetrachloride in the presence of both a source of metallic iron that is effective as an activator for the reaction, and a promoter for the reaction. According to a preferred embodiment, a reaction system is prepared comprising a liquid phase in contact with the source of metallic iron, the liquid phase comprising carbon tetrachloride and a promoter compatible therewith. Preferably, the promoter comprises a phosphorus (V) compound containing a phosphoryl group such as, for example, an alkyl phosphate, alkyl phosphonate, phosphoryl chloride, or phosphorus pentoxide. Trialkyl phosphates such as triethyl phosphate and tributyl phosphate are most preferred. Other particular phosphorus (V) compounds which can be used as the promoter for the reaction include dimethyl methylphosphonate, diethyl methylphosphonate, phenyl ethylphosphonate, phenyl butyl phosphate, dimethyl phenyl phosphate, and the like. Alternatively, but less preferably, a trialkyl phosphite such as triethyl phosphite or tributyl phosphite may be used as the phosphorus compound promoter for the reaction between ethylene and carbon tetrachloride. It has been found that higher productivity and yields are obtained with a trialkyl phosphate promoter as compared to trialkyl phosphite. Quality of the product is also generally better, and the reaction conditions less corrosive to process equipment.

A source of metallic iron effective as an activator for the reaction is necessary, along with the phosphorus promoter compound, to effect reaction of carbon tetrachloride with ethylene to produce the 1,1,1,3-tetrachloropropane with high selectivity, high yield and high productivity. Because the reaction is approximately first order with respect to the contact surface between the liquid phase and the source of metallic iron, it is preferred that iron sources having relatively large surface areas be used. Various sources of metallic iron can be used in the reaction, with carbon steel and wrought iron being preferred. Carbon steels are particularly advantageous. Cast iron is also suitable. Useful forms of the iron source include iron bars, rods, screens, filings, powder, sheets, wire, tubes, steel wool, and the like.

In order to maximize the selectivity of the reaction, it is further preferred that the liquid phase contain ferric chloride at the outset of the reaction. This can be achieved by either adding ferric chloride to the system or generating it in situ by heating the carbon tetrachloride in the presence of metallic iron and the promoter, preferably at about reaction temperature, prior to introduction of ethylene. Although the invention defined in the appended claims is not limited to a particular theory, it is believed that carbon tetrachloride is split into a trichloromethyl free radical and a chloride ion ligand by a redox transfer with ferrous ion, thereby producing a ferric ion to which the ligand is attached. It is further believed that the metallic iron serves as a source of ferrous ions that participate in the postulated redox transfer with carbon tetrachloride, and that the promoter is instrumental in the oxidation and dissolution of the metallic iron. Dissolution of metallic iron results in the formation of ferrous ions, either directly or by reduction of ferric ions in the liquid phase. Reaction of ethylene with the trichloromethyl radical produces a trichloropropyl radical that in turn condenses with the chloride ion ligand in a further redox transfer in which ferric ion is reduced to ferrous. Although ferric ion is thus produced in the course of the reaction by oxidation of ferrous ion, an initial concentration of ferric ion is useful in minimizing the formation of undesired by-products during the early stages of the reaction.

Where a phosphorus (V) compound is used as the promoter, it is also preferred that the ferric chloride be substantially anhydrous and that the reaction system be maintained substantially free of water throughout the reaction. In such systems, the presence of appreciable proportions of water significantly retards the reaction rate. However, where the promoter is a phosphite such as triethyl phosphite or tributyl phosphite, the presence of modest amounts of water is not disadvantageous. In fact, minor proportions of water, up to an amount stoichiometricly equivalent to the phosphite compound, may be useful in increasing the reaction rate. This may be due to the conversion of phosphites to phosphates and/or phosphonates, and the attendant formation of HCl in the case of phosphate formation, by reaction with carbon tetrachloride.

In carrying out the first step of the synthesis, ethylene is introduced into the carbon tetrachloride liquid phase containing the phosphorus compound, and preferably ferric chloride, in the presence of a source of metallic iron at a temperature of 50° C. to 150° C., preferably 70° C. to 130° C. As noted, the ferric chloride may be initially added as such or generated in situ by heating the CCl$_4$-promoter-Fe metal system prior to introduction of ethylene. Ethylene pressure is not narrowly critical. Typically, ethylene can be introduced at a gauge pressure of between about $1 \times 10^5$ Pa and about $14 \times 10^5$ Pa (about 1 and about 14 atmospheres). It has further been found desirable to have a relatively high ratio of ferric iron concentration to ethylene partial pressure. However, it is also important to maintain a molar excess of phosphorus compound with respect to ferric ion, since otherwise the reaction may stop. This is believed to result from the formation of a reaction product or 1:1 complex of phosphorus compound and iron ion. Although such reaction product or complex may still be active as a source of ferric ion for limiting the formation of $n \geq 2$ telomerization products, it appears to be inactive as a promoter for initiating the reaction. Preferably, therefore, the reactor charge should initially contain between about 0.1 mole % and about 5 mole % of the phosphorus compound and between 0 and about 2 mole % ferric chloride based on carbon tetrachloride.

Progress of the reaction depends on maintaining a supply of both free phosphorus compound and metallic iron throughout the reaction period. In order to assure the continued availability of phosphorus compound and metallic iron, it is, therefore, necessary to control not only the initial phosphorus compound and ferric chloride content, but also the overall quantity of metallic iron available for dissolution and also the area of contact between the liquid phase and the source of metallic iron. Intensity of agitation also affects this balance.

For any given system, those skilled in the art may readily arrive at an appropriate combination of these parameters. Preferably the system is operated with vigorous agitation and contains a quantity of iron sufficient to provide for several batches (or several multiples of residence time in a continuous system) without significant variation in surface area. This system both provides high productivity and facilitates maintenance of an effective supply of both phosphorus compound and metallic iron.

Further disclosure relevant to the preparation of 1,1,1,3-tetrachloropropane is set forth in the co-pending application of Scott S. Woodard, filed on July 6, 1983 under Ser. No. 511,130 which is herein expressly incorporated by reference.

Where the reaction of ethylene and carbon tetrachloride is catalyzed or promoted by a phosphorus (V) compound such as a trialkyl phosphate, in most instances the liquid product is substantially a single phase material containing a high proportion of 1,1,1,3-tetrachloropropane and can often be fed directly to the next step of the synthesis without further separation or purification. In the second step, the 1,1,1,3-tetrachloropropane is dehydrochlorinated by contacting it with a base, preferably an aqueous caustic solution, in the presence of a phase transfer catalyst. Preferably, the strength of the caustic solution is between about 15% and about 50% by weight. Phase transfer catalysts useful in this reaction are known to the art. For example, various quaternary ammonium and quaternary phosphonium salts can be used to promote this dehydrochlorination step. The dehydrochlorination is preferably carried out by slowly adding the caustic solution to 1,1,1,3-tetrachloropropane containing the phase transfer catalyst while agitating the reaction mixture at a temperature of 40° C. to 80° C., preferably 50° C. to 75° C. After addition of the caustic solution is complete, the mixture is stirred for an additional period at reaction temperature and then cooled. The aqueous phase is separated and discarded. The organic phase containing a mixture of 1,1,3- and 3,3,3-trichloropropene may then be used directly in the next step of the synthesis.

In the next synthesis step, the trichloropropene mixture is chlorinated, preferably in the presence of ultraviolet light to produce 1,1,1,2,3-pentachloropropane. Chlorine gas may be introduced either above the liquid surface or through a dip pipe and sparger. Chlorination temperature is not critical but may typically range from $-10°$ C. to $+80°$ C., preferably 0° C. to 65° C. Preferably the isomeric mixture of 1,1,3- and 3,3,3-trichloropropenes is chlorinated directly to produce 1,1,1,2,3-pentachloropropane. Alternatively, the trichloropropene isomers can be separated prior to chlorination of one or both of them, or the 3,3,3- isomer component thereof first converted to the 1,1,3-isomer by contact with a Lewis acid allylic rearrangement catalyst. If $FeCl_3$ is used for the rearrangement reaction, it should be removed prior to chlorination, as by distilling the isomerized material or extracting the $FeCl_3$.

1,1,1,2,3-pentachloropropane is converted to an isomeric mixture of 2,3,3,3- and 1,1,2,3-tetrachloropropene by dehydrochlorination with a base, preferably an aqueous caustic solution, in the presence of a phase transfer catalyst. Generally, the catalyst and caustic strengths used in this step may be approximately the same as those used in the dehydrochlorination of 1,1,1,3-tetrachloropropane. As in the earlier dehydrochlorination step, caustic solution is added slowly to the pentachloropropane containing the phase transfer catalyst. However, the temperature used in this step may be somewhat higher than in the second step, i.e., in the range of 70° C. to 110° C., preferably 80° C. to 100° C. After all caustic is added, the reaction mixture is cooled, the phases separated and the aqueous phase discarded. The organic phase containing an isomeric mixture of 2,3,3,3- and 1,1,2,3-tetrachloropropene may be distilled prior to the isomerization step.

To carry out the final step of the synthesis, the isomeric mixture of tetrachloropropenes is mixed with a Lewis acid allylic rearrangement catalyst which effects rearrangement of 2,3,3,3- to 1,1,2,3-tetrachloropropene. However, if there is perceptible water in the isomerization mixture, as indicated, for example, by cloudiness or the presence of drops, or if a hydrated catalyst is used, the mixture is preferably subjected to azeotropic distillation to remove residual water. Isomerization may proceed concomitantly with moisture removal, accelerating as the water content of the mixture declines.

Although other Lewis acid catalysts are known to be effective, it is particularly preferred that the isomerization reaction be carried out using substantially anhydrous ferric chloride as the catalyst.

It has been discovered that anhydrous ferric chloride catalyzes a very rapid allylic rearrangement of 2,3,3,3-tetrachloropropene to 1,1,2,3-tetrachloropropene without affecting the 1,1,2,3- isomer initially present or formed in the rearrangement reaction. Moreover, the catalytic proportion of ferric chloride needed for the step is quite low, for example, as low as 5 ppm. Higher concentrations promote more rapid reaction, but concentrations above about 5% by weight do not serve a useful purpose. In fact, where the 1,1,2,3-tetrachloropropene is used for the preparation of triallate, relatively large proportions of $FeCl_3$ in the 1,1,2,3-tetrachloropropene, for example 500 ppm or more, may lead to formation of ferric hydroxide which must be separated from the triallate. For this reason, $FeCl_3$ concentration for catalyzing the rearrangement is preferably limited to 5 ppm to 400 ppm. Also, because the rearrangement is highly exothermic, catalyst dosage and initial reaction temperature should be adjusted to avoid an excessive temperature rise. Temperature increases of 80° C. or higher can be experienced. For this reason, a diluent may also be desirable, for example, a heel of product from a prior batch.

It has further been found that the 1,1,2,3-tetrachloropropene produced in the isomerization step can be utilized directly without further purification in the synthesis of the herbicide triallate. Triallate is produced by reaction of 1,1,2,3-tetrachloropropene with diisopropylamine, carbonyl sulfide and a base.

In an alternative embodiment of the invention, 1,1,1,2,3-pentachloropropane is converted directly to 1,1,2,3-tetrachloropropene by dehydrochlorination utilizing ferric chloride as a dehydrochlorination catalyst. In this embodiment of the invention, the 1,1,1,2,3-pentachloropropane is contacted with a catalytic proportion of ferric chloride. Preferably the dehydrochlorination reaction is carried out at a temperature of between about 70° C. and about 200° C. The proportion of ferric chloride utilized in the reaction is preferably between about 0.05% and about 2% by weight of the 1,1,1,2,3-pentachloropropane. When the dehydrochlorination is carried out in this fashion, hydrogen chloride gas is given off. This off gas may be either absorbed in water or used directly in other operations. Conversion to 1,1,2,3-tetrachloropropene is essentially quantitative. Isomers of the desired product are either not formed or are immediately converted to the 1,1,2,3-isomer via an allylic rearrangement reaction as catalyzed by the ferric chloride present.

Whichever route is followed for conversion of 1,1,1,2,3-pentachloropropane, simplified operation is realized at high productivity and yield where each of the several steps of the processes of the invention is run to essentially complete conversion. However, some deterioration in yield is typically experienced at very high conversions in the dehydrochlorination of 1,1,1,3-tetrachloropropane. Typically, the incidence of by-product formation may increase to a significant level at conversions above 70%. In an alternative embodiment of the invention, therefore, conversion and/or by-product formation is monitored and addition of caustic solution terminated so as to limit the conversion to 80% to 90%. The desired product can be separated from unreacted 1,1,1,3-tetrachloropropane and the various by-products by fractional distillation following phase separation. Alternatively, the organics may be taken over by steam distillation without prior phase separation, and the takeover product fractionated. Optionally, the aqueous phase may be neutralized or acidified prior to steam distillation. In a still further embodiment, the trichloropropenes can be removed from the reaction as they are formed by fractional steam distillation.

Unreacted 1,1,1,3-tetrachloropropane is recycled to the dehydrochlorination step.

The following examples illustrate the invention.

EXAMPLE 1

Carbon tetrachloride (273 g), triethyl phosphate (4.05 g), ferric chloride (1.03 g), and two mild steel rods having a total surface area of 26 cm$^2$ were charged to a 300 ml Hastelloy C autoclave provided with an internal cooling coil. The autoclave was thereafter flushed twice with nitrogen and once with ethylene, pressurized with ethylene to about $4.1 \times 10^5$ Pa gauge (4.1 atm gauge), and sealed. The mixture contained in the autoclave was stirred at 600 rpm and heated to 120° C., at which temperature the pressure was observed to be approximately $8.3 \times 10^5$ Pa gauge (8.2 atm gauge). As a result of the reaction of the carbon tetrachloride with the ethylene, the pressure in the clave dropped rapidly. Within one minute of reaching 120° C., the ethylene feed valve was reopened and the autoclave pressurized to about $9.8 \times 10^5$ Pa gauge (9.7 atm gauge) and maintained there for 150 minutes. The reactor was then cooled and vented. A product mixture (327 g) was obtained. No tars or solids were produced. However, a slight second phase did separate upon standing. The product mixture was analyzed and found to contain 95.1% by weight of 1,1,1,3-tetrachloropropane. Only 0.4% carbon tetrachloride remained. The yield based on carbon tetrachloride initially present was 96.4%. The mild steel rods were weighed and it was determined that 0.54 g of iron had dissolved in the reaction mixture during the course of the reaction. A repeat of this reaction required 190 minutes to reach completion and the yield was 96.6%.

EXAMPLE 2

Carbon tetrachloride (806 g), triethyl phosphite (8.8 g), acetonitrile (2.16 g), and ferric chloride hexhydrate (1.41 g) were charged to a one liter stainless steel autoclave equipped with a stirrer, cooling coil and condenser. The autoclave was flushed with nitrogen and then charged with ethylene to a gauge pressure of about $4.8 \times 10^5$ Pa gauge (4.8 atm gauge) while stirring the liquid charge. The liquid contents of the autoclave were heated to 120° C. As heating took place, the pressure rose to a peak of about $9.3 \times 10^5$ Pa gauge (9.2 atm gauge) and then began to drop as the temperature approached 120° C. When the temperature reached 120° C., the autoclave was pressurized to about $9.8 \times 10^5$ Pa gauge (9.7 atm gauge) with ethylene and the reacting mixture maintained at 120° C. and stirred for six hours at that ethylene pressure. After six hours the reactor was cooled, then vented. The liquid product collected from the autoclave weighed 952 g, of which 887 g was identified as 1,1,1,3-tetrachloropropane (93.1% yield). No unreacted carbon tetrachloride was detected in the product, indicating a 100% conversion. Slight tar formation on the reactor cooling coils was noted.

EXAMPLE 3

Carbon tetrachloride (278 g), triethyl phosphate (4.05 g) and two mild steel rods having a total surface area of 26 cm$^2$ were charged to a 300 ml Hastelloy C autoclave. The autoclave was thereafter flushed twice with nitrogen, then once with ethylene, pressurized with ethylene to about $3.4 \times 10^5$ Pa gauge (3.4 atm gauge), and sealed. The mixture contained in the autoclave was stirred and heated to 120° C. at which temperature the gauge pressure was observed to be approximately about $9.6 \times 10^5$ Pa gauge (9.5 atm gauge). As a result of reaction of the carbon tetrachloride with ethylene, the pressure in the autoclave then dropped rapidly and, when the pressure dropped below about $6.9 \times 10^5$ Pa gauge (6.8 atm gauge), the ethylene feed valve was reopened, the autoclave repressurized to about $6.9 \times 10^5$ Pa gauge (6.8 atm gauge) and maintained at that presssure for a total of four hours. The reactor was then cooled and vented. The product mixture (331 g) was analyzed and found to contain 93.5% by weight 1,1,1,3-tetrachloropropane. Only 0.6% carbon tetrachloride remained. The yield based on the carbon tetrachloride initially present was 94.2%. The mild steel rods were weighed and it was determined that 0.81 grams of iron had dissolved in the reacting mixture during the course of the reaction.

EXAMPLE 4

Carbon tetrachloride (265 g), triethyl phosphate (4.18 g), and two mild steel rods having a total surface area of 26 cm$^2$ were charged to the autoclave described in Example 1. The autoclave was thereafter flushed three times with nitrogen and sealed. The mixture contained in the autoclave was stirred at 600 rpm and heated to 120° C., at which point the pressure was approximately 3.2×10$^5$ Pa gauge (3.2 atm gauge). After the mixture had been heated at 120° C. for 37 minutes, the ethylene feed valve was opened and the autoclave pressurized to 6.9×10$^5$ Pa gauge (6.8 atm gauge) and maintained at that pressure for 280 minutes. After 208 minutes of ethylene addition, 1.07 g of additional triethyl phosphate was charged to the autoclave, resulting in an increased reaction rate at that point, thereby effecting substantially complete reaction after a total of 280 minutes of ethylene addition. The reactor was cooled and vented. A product mixture (317 g), similar in nature to that in Example 1, was obtained. No tars or solids were produced. The product mixture upon analysis was found to contain 94.3% by weight 1,1,1,3-tetrachloropropane. Only 0.4% carbon tetrachloride remained. The yield based on carbon tetrachloride initially present was 96.2%. The mild steel rods were weighed and it was determined that 0.95 g of iron had dissolved in the reaction mixture during the course of the reaction.

EXAMPLE 5

1,1,1,3-tetrachloropropane (149 g; approximately 100% pure) and a tetraalkyl quaternary ammonium halide sold under the trade designation Aliquat 336 by General Mills (0.54 g) were charged to a 500 ml ACE reactor having side indents and provided with a thermometer, mechanical stirrer and addition funnel. The addition funnel was charged with 50% sodium hydroxide solution (66.5 g) that had been diluted to approximately 140 ml (approximately 20% caustic). The mixture in the reactor was stirred and heated on a steam bath to 65° C. When the temperature reached 65° C., slow addition of caustic solution was commenced and this addition was continued over a period of 70 minutes. During caustic addition, the reaction temperature was maintained at 67°±2° C. When addition of caustic was complete, the reaction mixture was stirred for an additional 36 minutes at 67° C. Stirring was then stopped and the mixture cooled. The aqueous phase was removed and the product organic phase determined to weigh 120 g, of which 55.1 g (51.8% yield) was 3,3,3-trichloropropene, 35.6 g (42.8% yield) was 1,1,3-trichloropropene, and 16.3 g was unreacted 1,1,1,3-tetrachloropropane (89.1% conversion).

The organic phase obtained from the reaction was distilled to provide a mixture of 3,3,3- and 1,3,3-trichloropropene of about 98.8% purity and containing a ratio of approximately 55 parts 3,3,3-isomer to 45 parts 1,1,3-isomer.

EXAMPLE 6

A portion of the mixture of 3,3,3- and 1,1,3-trichloropropene prepared in Example 3 (66.0 g) was charged to a three-neck 100 ml round bottom flask equipped with a magnetic stir bar, an ultra violet lamp and two gas ports. The flask was then placed on an ice bath and the isomer mixture cooled to 0° C. While the contents of the flask were stirred and irradiated with ultra violet light, chlorine was fed into the flask via one of the gas ports at such rate that a small but detectable amount exited the other gas port. Exit flow was detected by use of a gas bubbler. The chlorine input port was above the liquid surface. At intervals the reaction mixture was sampled to determine completeness of chlorination. After 36 minutes, all of both of the trichloropropene isomers were consumed, yielding 1,1,1,2,3-pentachloropropane in essentially 100% conversion. 98.7 g of organics were collected from the flask of which 93.8 g (96.8% yield) was 1,1,1,2,3-pentachloropropane.

EXAMPLE 7

A 500 ml ACE reactor with side indents, equipped with a mechanical stirrer, addition funnel and thermometer, was charged with 1,1,1,2,3-pentachloropropane (145 g; 97.4% pure) and Aliquat 336 (0.31 g). The addition funnel was charged with a 50% caustic solution (55.2 g) which had been diluted to a volume of approximately 130 ml. The mixture contained in the reactor was stirred and heated via a steam bath to a temperature of 90° C. and held at 90°±2° C. throughout the subsequent reaction. When the contents of the reactor reached 90° C., slow addition of caustic solution was commenced and continued over a period of two and one-half hours and then held for another one-half hour. The reaction mixture was cooled down, stirring terminated and the organic and aqueous phases separated. 118 g of organics was collected, of which 115 g (98.0% yield) was an isomer mixture of 2,3,3,3- and 1,1,2,3-tetrachloropropene. No 1,1,1,2,3-pentachloropropane was detected in the collected organic phase, indicating that the conversion was 100%.

EXAMPLE 8

The organic phase produced in accordance with Example 5, comprising an approximately 55/45 mixture 2,3,3,3- and 1,1,2,3-tetrachloropropene and containing no visible water (no cloudiness or drops), was mixed with 0.17% by weight anhydrous ferric chloride. This mixture was heated at 103° C. for 15 minutes. Quantitative isomerization of 2,3,3,3- to 1,1,2,3-tetrachloropropene was achieved.

EXAMPLE 9

A one liter round bottom flask equipped with a condenser and collector was charged with a mixture containing approximately a 45/55 ratio of 1,1,2,3-tetrachloropropene to 2,3,3,3-tetrachloropropene and 2.3 ml of a 1% aqueous ferric chloride solution. The mixture was heated to reflux, and the water azeotroped into the collector. All organics collected were returned to the flask. Within minutes of reaching reflux and removal of the water, quantitative isomerization took place converting all of the 2,3,3,3-tetrachloropropene into 1,1,2,3-tetrachloropropene.

EXAMPLE 10

A dry 100 ml round bottom flask equipped with a condenser and magnetic stir bar was charged with 94.5 g of 1,1,1,2,3-pentachloropropane (92.4% pure) and 0.26 g of ferric chloride. The mixture was heated and stirred at 164° C. for 7 hours. HCl gas was evolved during the reaction and was absorbed directly into water. After cooling down, 79.3 g of product mixture was obtained. This was analyzed and found to contain 93.5% by weight 1,1,2,3-tetrachloropropene and 0.58% by weight starting material. This corresponds to conversion of 99.5% and an essentially quantitative yield.

As various changes could be made in the above methods without departing from the scope of the invention, it is intended that all matter contained in the above description shall be interpreted as illustrative and not in a limiting sense.

What is claimed is:

1. A process for producing 1,1,2,3-tetrachloropropene comprising the steps of:

preparing 1,1,1,3-tetrachloropropane by reacting ethylene with carbon tetrachloride in the presence of both a source of metallic iron that is effective as an activator for the reaction, and a promoter for the reaction, said promoter being selected from phosphorus (V) compounds containing a phosphoryl group;

dehydorchlorinating said 1,1,1,3-tetrachloropropane to produce a mixture of 1,1,3- and 3,3,3-trichloropropenes;

chlorinating at least one of the trichloropropenes obtained by said dehydrochlorination of 1,1,1,3-tetrachloropropane to produce 1,1,1,2,3-pentachloropropane;

dehydrochlorinating the 1,1,1,2,3-pentachloropropane to produce a mixture of 1,1,2,3- and 2,3,3,3-tetrachloropropenes; and contacting the mixture of tetrachloropropenes with a rearrangement catalyst, thereby converting the 2,3,3,3-tetrachloropropene content thereof to 1,1,2,3-tetrachloropropene.

2. A process as set forth in claim 1 wherein said phosphorus (V) compound is selected from the group consisting of alkyl phosphates and alkyl phosphonates.

3. A process as set forth in claim 1 wherein the reaction between ethylene and carbon tetrachloride is carried out in a reaction system comprising a liquid phase in contact with said source of metallic iron, said liquid phase comprising carbon tetrachloride and said promoter, said promoter being compatible with said carbon tetrachloride.

4. A process as set forth in claim 3 wherein said liquid phase contains ferric chloride prior to the initiation of said reaction.

5. A process as set forth in claim 4 wherein said phosphorus (V) compound is initially present in molar excess with respect to ferric chloride.

6. A process as set forth in claim 1 wherein said rearrangement catalyst comprises ferric chloride.

* * * * *